United States Patent [19]

Wagner et al.

[11] Patent Number: 4,776,792
[45] Date of Patent: Oct. 11, 1988

[54] DENTAL ARCH OCCLUSAL SURFACE PRINT RECORDING PALLET AND PROCESS OF USING THE SAME

[75] Inventors: John W. Wagner, Seattle; Michael A. Knight, Edmonds, both of Wash.

[73] Assignee: Oral Dynamics, Inc., Edmonds, Wash.

[21] Appl. No.: 15,836

[22] Filed: Feb. 18, 1987

[51] Int. Cl.⁴ .............................................. A01C 9/00
[52] U.S. Cl. .......................................... 433/71; 433/37
[58] Field of Search ............................. 433/71, 229, 37

[56] References Cited

U.S. PATENT DOCUMENTS

| | | | |
|---|---|---|---|
| 1,346,998 | 7/1920 | Veale | 433/35 |
| 3,303,844 | 2/1967 | Johnson et al. | 128/136 |
| 3,473,225 | 10/1969 | Deuschle et al. | 32/17 |
| 4,044,762 | 8/1977 | Jacobs | 128/136 |
| 4,401,616 | 8/1983 | Wagner | 264/138 |
| 4,508,156 | 4/1985 | Banks et al. | 433/71 |
| 4,580,977 | 4/1986 | Ames | 433/229 |
| 4,676,748 | 6/1987 | Pietkivitch | 433/71 |

FOREIGN PATENT DOCUMENTS 1681690 2/1954 Fed. Rep. of Germany .
2512443 9/1976 Fed. Rep. of Germany .

Primary Examiner—Robert Peshock
Attorney, Agent, or Firm—Robert W. Beach; Ward Brown

[57] ABSTRACT

A print pallet composed of a dental tray holding a filler pad of thermoplastic material can be warmed to plasticize such material and inserted into the mouth of a person to be identified to be stamped by the occlusal surfaces of that person's dental arch to imprint a print of such arch occlusal surfaces on the pad. Such print record can be preserved or recorded by various media for later comparison to establish the identity of the person when deceased or incapacitated.

5 Claims, 1 Drawing Sheet

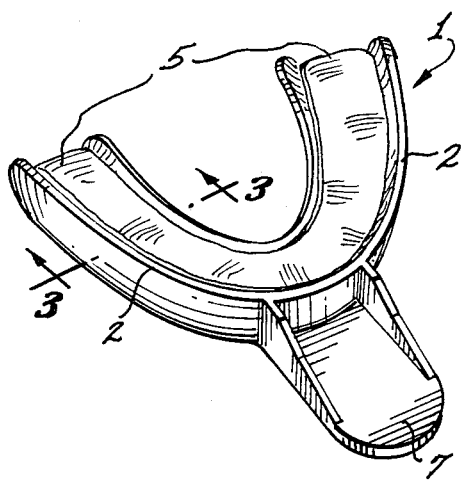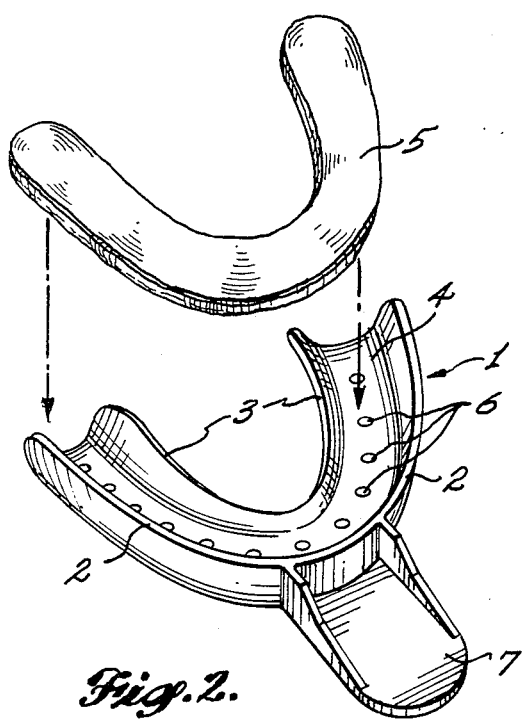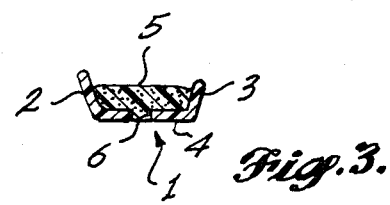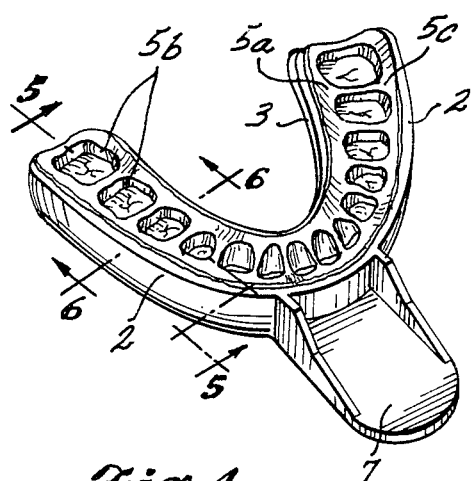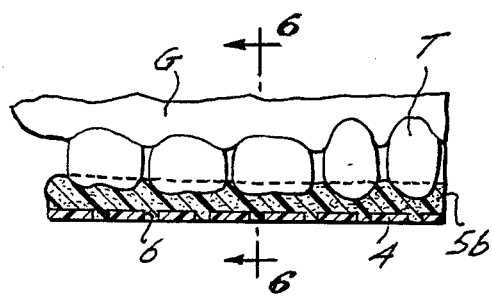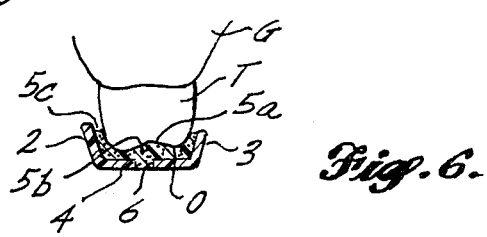

DENTAL ARCH OCCLUSAL SURFACE PRINT RECORDING PALLET AND PROCESS OF USING THE SAME

BACKGROUND OF THE INVENTION

1. Field of the Invention

This invention relates to pallets for making prints of dental arch occlusal surfaces for identification purposes.

2. Problem

The most certain customary expedient for identifying persons is fingerprints. Fingerprints are generally satisfactory for identifying living individuals but are frequently ineffective for identifying deceased victims of a tragedy such as a fire or a situation in which the remains have degenerated over a sufficient period of time that fingerprints of the deceased can no longer be taken.

When fingerprinting technique is not available to identify deceased persons resort is frequently had to dental records. Such records are of assistance in identifying a deceased person if the identity of such person is suspected so that the appropriate dentist can be located and his records of the presumed prior patient checked. This technique is of little or no value, however, where there is no clue to the possible identity of the deceased person.

The problem solved by the present invention is to provide an article and a procedure which can be used for identifying a living person and which identification can be made of record so as to be readily available for identifying deceased persons even if the identity of such persons is not suspected and even if the condition of the body of the deceased is such that fingerprints cannot be taken.

SUMMARY OF THE INVENTION

A principal object of the invention is to provide a practical record and procedure to establish the identity of living individuals which record will remain available for identifying such individuals when they have become deceased under such circumstances that fingerprints cannot be taken of the deceased persons, such as when they have been victims of a fire.

More specifically, it is an object of the present invention to provide identification for persons both living and deceased by recorded prints of a dental arch occlusal surface relief.

A still more specific object is to provide articles and procedure which will record accurately the contour of occlusal surfaces and tooth spacing in dental arches.

It is also an object to provide an article with which identification dental arch occlusal surface relief records can be made quickly and easily.

A specific object is to utilize an article for recording prints of dental arch occlusal surface reliefs which is of thermoplastic character that can be rendered plastic easily and quickly for making the identifying print record and then can be hardened reliably and quickly to fix the print.

It is a further object to utilize material for making such a print which is shape and dimensionally stable so that both the size and shape of the print will be preserved unchanged for an extended period of time.

An additional object is to provide such print material that is not sticky when in plastic condition and can be separated easily from teeth, or on which a parting material or coating can be used to insure ready parting of the print from the teeth.

Another object is to provide an article in which the identification print is substantially only of the occlusal surfaces of the teeth and the teeth cannot be embedded in the recording material to an extent which would produce any substantial negative draft that would appreciably deter withdrawal of the completed print from the teeth.

It is also an object to minimize the amount of thermoplastic material required for making the identification print.

A further object is to provide a holder for the identification print material when it is in plastic condition so that such material can be manipulated easily and can be supported against deformation until it has been hardened following the record imprinting procedure.

To minimize inventory, it is also an object to provide articles which can be used for recording the occlusal surface relief of either the upper dental arch or the lower dental arch.

The foregoing objects can be accomplished by providing a composite dental arch occlusal surface relief print pallet including a generally planar trough-shaped tray of arch shape having a substantially flat web with a narrow concave flange upstanding from the inner edge of the web and a narrow convex flange upstanding from the outer edge of the web, having a handle projecting mesially outward from the outer flange and disposed substantially coplanar with the arch trough, and which trough has in it a thin pad of thermoplastic material to be imprinted by the occlusal surface relief of a dental arch.

PRIOR ART

The print pallet of the present invention utilizes a holder or tray generally similar to the dental impression tray of the type shown in FIGS. 1 to 4 of U.S. Pat. No. 3,473,225, issued Oct. 21, 1969, but differing in proportions, principally in the height of the internal concave and external convex flanges of the tray trough.

The thermoplastic material of which the pad lodged in the trough of the holder is made can be like that described in U.S. Pat. No. 4,401,616, issued Aug. 30, 1983, at column 4, lines 53 to 62, as follows:

The thermoplastic flat sheet material manufactured by Rolyan Manufacturing Co. Inc. of Menomonee Falls, Wisconsin, under its trademark "Polyform" in a thickness of about ⅛ inch (3.2 mm) meets all of the above requirements and is the preferred material to be used in practice of the present invention. It is substantially rigid or hard and tough at body and ambient temperatures but is deformable, nonresilient and nonliquid when heated to a temperature between about 145° F. (71° C.).

The article disclosed in that patent is quite different from the article of the present invention, however, in that the article of that patent is a custom dental tray conforming only approximately to the contour of a dental arch, whereas the present invention involves making a precise and detailed print of the occlusal surface of a dental arch.

While German publication No. 25 12 443, published Sept. 30, 1976, discloses apparatus for preparing impressions for dentures, this patent also discloses the making of a custom tray having a space-holder layer 12 generally complemental to the teeth of a dental arch, but such space-holder layer is not precise and detailed and is only utilized to provide space of approximately uniform thickness for receiving deformable refined impression material to be inserted into the preliminary impression of the custom tray after the removal of the space-holder layer, as stated on page 2 of this German publication.

The apparatus of this patent is for the purpose of taking impressions for a denture so that it must conform to the entire height of the teeth and an area of the gums around the roots of the teeth, as indicated in FIG. 4. The final impression 17 constitutes a precise adaptation of the refined impression material 16 to the teeth 14 and the jaw 15, as stated at the middle of page 9 of the English translation of the reference. After the refined impression material 16 has set, the preliminary impression material 11 and the refined impression material 16 having the final impression 17 is removed from the teeth 14 and the jaw 15 and is taken out of the mouth of the patient, as stated near the bottom of page 9 of the English translation of the German reference.

German Utility Model No. 1 681 690, dated Feb. 18, 1954, shows an impression sheet B, C that can be deformed in the mouth to produce an impression tray a and FIG. 4 shows the production of the impression tray in the case of a toothed jaw. This utility model states in the second full paragraph on page 4 of the English translation that for a toothed jaw thermoplastic material produces an impression tray which has a corresponding depression for reception of impression material for the production of a negative impression. It is clear from FIG. 4 that, in this case also, the final impression material fills the space around the entire depth of the tooth and the adjacent portions of the gum. This patent likewise, therefore, shows an article which is quite different from the article of the present invention and is used in a different manner for a different purpose.

The production of mouth guards involves different considerations from those of the present invention. U.S. Pat. No. 3,303,844, issued Feb. 14, 1967, relates to the production of a mouth guard which closely fits about the teeth, as stated at column 1, lines 20 and 21, and lines 30 and 31, and also about the gum tissue, as stated at column 2, lines 40 and 41, instead of the article having an imprint of substantially only the occlusal teeth surfaces of a dental arch. Further, instead of the material of the mouth guard being thermoplastic, it is cured at a temperature in the neighborhood of 300° F. (148.89° C.) to 400° F. (204.44° C.) (column 2, lines 36 to 38) and when cured can be subjected to boiling water without softening (column 4, lines 2 and 3). Even when cured, however, the mouth guard material is not hard but is cured from the soft putty state to a tough elastic state, as stated at column 2, lines 32 to 34, rather than being hard (column 4, line 6).

U.S. Pat. No. 4,044,762, issued Aug. 30, 1977, discloses a mouthguard made of thermoplastic resin which can be softened in hot water, as stated at column 1, lines 55 to 57, but this mouthguard also is formed to conform to the wearer's teeth and surrounding gum tissue, as stated at column 2, lines 25 and 26, instead of providing a print of substantially only the occlusal tooth surfaces of the dental arch.

BRIEF DESCRIPTION OF THE DRAWINGS

FIG. 1 is a top perspective of the dental arch occlusal surface print pallet of the present invention before use, and FIG. 2 is a corresponding view of such pallet showing components in exploded relationship.

FIG. 3 is a vertical section through a portion of the pallet taken on line 3—3 of FIG. 1.

FIG. 4 is a top perspective of the pallet shown after a print of a dental arch occlusal surface relief has been stamped on the pallet.

FIG. 5 is a fragmentary circumferential section through a portion of the pallet shown in FIG. 4 taken along 5—5 of that figure located in the mouth during the process of producing an occlusal surface print on the pallet.

FIG. 6 is a generally radial section through the pallet taken on line 6—6 of FIG. 4 and line 6—6 of FIG. 5.

DETAILED DESCRIPTION

The composite arch-shaped pallet for making dental arch occlusal surface record prints is shown in FIGS. 1 to 6 of the drawings. A component par of the pallet is the arch-shaped tray generally designated 1 in FIGS. 1 and 2 having a convex outer flange 2 and a concave inner flange 3 projecting in the same direction from opposite edges of the tray bottom or web 4. The tray is of a size and has a contour to fit a reasonable range of sizes of both upper jaws and lower jaws.

As shown in FIG. 3, it is preferred that the inner flange 3 of the tray be narrow and narrower than the convex outer flange 2. Both flanges are sufficiently narrow, however, that their combined width is less than the radial width of the trough web or bottom 4. Within the trough is lodged a thin arch-shaped filler pad 5 of thermoplastic material which material may be of the type disclosed in U.S. Pat. No. 4,401,616 as discussed above. The tray 1 is made of conventional hard strong plastic material which is not appreciably thermoplastic at softening temperatures of the pad material. The thickness of the thermoplastic material pad 5 should not be appreciably, if any, greater than the width of the flange 3, and the flange 2 is preferably wider than the thickness of the pad. Also, the pad thickness should be less than one-half of the radial width of such pad and not appreciably greater than about twice the thickness of the tray, as shown in FIG. 3. The pad should have a thickness which is a minor portion of the distance between the tooth occlusal surface and the gum line, such as being ⅛ to 3/16 inch (3.17 to 4.77 mm) in thickness.

The tray 1 and pad 5 could be supplied to a user as separate components of the composite pallet, but it is preferred that these two components be supplied as a unit. The pad can be integrated with the tray by providing apertures 6 in the tray bottom into which projections from the pad can be extruded by pressure applied to the upper surface of the pad in thermoplastic condition when it is lodged in the tray. To increase the grip of the apertures 6 on the projections extruded from the pad, such apertures can be flared outwardly.

To facilitate handling of the pallet, a handle 7 may be provided which projects generally radially of the arch from the mesial portion of the outer flange 2 and preferably is disposed generally coplanar with the tray.

In order to record a dental arch occlusal surface, a print of such surface is made on the exposed principal face of the pad 5 by placing the pallet in the person's mouth with the pad principal face facing up if the print is to be made of the upper dental arch occlusal surface and with the pad principal face facing downward if the print is to be made of the lower dental arch occlusal surface so that the print record will be stamped on the principal face of the pad.

Prior to placing the filled tray in the person's mouth, it is heated sufficiently to plasticize the pad 5, but not the tray 1, such as by dipping the pallet in hot water in excess of about 145° F. (62.78° C.) for a few seconds, such as 5 seconds to 15 seconds, depending on the temperature of the water. The pad should be immersed for a longer period, such as 15 seconds, if the temperature of the hot water is 145° F. (62.78° C.), or a shorter period, such as 5 seconds, if the temperature is close to boiling, such as over 200° F. (93.33° C.).

With the thermoplastic pad 5 plasticized, the dentist or other operator places the pallet in an appropriate position in the person's mouth by grasping the handle 7 to manipulate the pallet. The person having the print made then closes his jaws reasonably slowly to a position in which the occlusal surfaces of all or most of the teeth in the dental arch are stamped on the exposed principal surface of the pad, as shown in FIGS. 5 and 6. The person then opens his mouth to release the pallet which is withdrawn by the operator from the person's mouth and bears the negative print of substantially only the occlusal surfaces of the dental arch as shown in FIG. 4. The material of the pad will be impressed accurately in detail by the occlusal surfaces of the teeth and is not sticky when in plasticized condition so that it can be separated easily from the teeth.

When the pallet bearing the print of the dental arch occlusal surface has been removed from the person's mouth it is chilled to restore the rigidity and hardness of the material. Such chilling can be effected by dipping the pallet in cold water to harden the imprinted pad quickly. Until the pad 5 has thus been hardened, the tray 1 forms a holder for the pad even when it has been heated to plasticize the thermoplastic material. The entire pad-softening, tooth arch occlusal surface imprinting and pad-rigidifying procedure can be accomplished in less than one minute.

When the thermoplastic material has been chilled, it becomes hard and strong and can be handled and even sent through the mail without the tray 1 with little risk of deforming or breaking the print. It is preferred, however, that the tray and pad constitute an integral unit in which the pad is not removed from the tray, but these two components will remain locked together and can be handled and shipped as a unit. The hardened plastic is shape and dimensionally durably stable at ambient temperatures over at least many years.

For making such an occlusal surface print, the pad 5 should be of a sufficient thickness so that during the imprinting process the occlusal surfaces or incisal portions of each tooth will perform the imprinting or stamping operation, but the plastic material should not be squeezed appreciably, if at all, beyond the occlusal surface, as shown in FIG. 6. The tray flanges 2 and 3 should be wide enough to prevent the material of the pad in plastic condition from being squeezed over the edges of the flanges, but, as is evident from FIG. 5 and FIG. 6, the average depth of penetration of each tooth into the pad 5 is a minor portion of the height of the tooth between the occlusal surface of the teeth T and the gum G. Such average depth of each tooth print preferably also is a minor portion, i.e., less than half, of the circumferential marginal width of the respective tooth print. Moreover, as shown in FIGS. 5 and 6, the maximum depth of the imprint depression is not appreciably in excess of twice the depth of the occlusal surface depressions because the purpose of the tooth print is to record the contour of the occlusal surfaces and the tooth spacing without taking an impression of a substantial portion of the side surfaces of the teeth.

In making the occlusal surface print, as shown in FIG. 6, the pad 5 is stamped to the representative shape 5a having an exposed surface 5b that is complemental to the occlusal surface of the tooth T. A portion of the pad material 5c may be squeezed alongside the tooth but such portion is of little or no significance to the occlusal surface print record.

It is important that the thermosetting material pad 5 be heated sufficiently so that its surface 5b will be imprinted precisely and in detail with substantially the full occlusal surface of each tooth T. Such print will be unique for each person with respect to both the contour of the print that engaged the occlusal surface of the tooth and also with respect to the spacing and otherwise positioning of adjacent teeth in the dental arch so that such print record or any data recorded from such print can be compared in the future with a later print of dental arch occlusal surfaces of a deceased or incapacitated person.

We claim:

1. A composite pallet for recording a print of dental arch tooth occlusal surfaces comprising a pad of thermoplastic material softenable by warming to a temperature of about 145° F. (62.78° C.) to a plasticized nonsticky condition deformable into intimate detailed contact with such tooth occlusal surfaces and quickly hardenable by cooling to durable rigid hard strong condition , dimensionally stable for preserving accurately the shape of the print of such tooth occlusal surfaces, and a tray of hard strong material which is not softenable at such softening temperature of said pad, having one side overlaid by said pad and without a pad overlying its opposite side, said pad having a thickness a minor portion of the distance between the occlusal surface and the gum of a tooth in the dental arch and providing an exposed principal face for reception of a print of substantially only the dental arch tooth occlusal surfaces.

2. A composite pallet for recording a print of dental arch tooth occlusal surfaces comprising a curved generally planar pad of thermoplastic material softenable by warming to a temperature of about 145° F. (62.78° C.) to a plasticized nonsticky condition deformable into intimate detailed contact with such tooth occlusal surfaces and quickly hardenable by cooling to durable rigid hard strong condition, dimensionally stable for preserving accurately the shape of the print of such tooth occlusal surfaces, and a tray of hard strong material which is not softenable at such softening temperatures of the said curved pad, having one side overlaid by said pad and without a pad overlying its opposite side, said curved pad having a thickness a minor portion of its radial width and providing an exposed principal face for reception of a print of substantially only the dental arch tooth occlusal surfaces.

3. A composite pallet recording of a print of dental arch tooth occlusal surfaces comprising a pad of thermoplastic material softenable by warming to a temperature of about 145° F. (62.78° C.) and quickly hardenable by cooling to durable rigid hard strong condition, dimensionally stable for preserving accurately the shape of the print of such tooth occlusal surfaces, and a tray having one side overlaid by said pad to provide an exposed principal face which bears a print of substantially only tooth dental arch occlusal surfaces having tooth print depressions and without a pad overlying the opposite side of said tray, the maximum depth of the tooth imprint depression in such principal face not appreciably exceeding twice the maximum depth of the occlusal surface depressions.

4. A process for recording a print of dental arch tooth occlusal surfaces on a pad of thermoplastic material softenable by warming to a temperture of about 145° F. (62.78° C.) and hardenable by cooling, which pad overlies a rigid tray of hard strong material which is not softenable at such softening temperature of the pad to form a pallet having an exposed principal print-receiving surface, which process comprises warming the pallet and thereby softening the pad material but not the tray material, inserting the pallet into a person's mouth, stamping the dental arch tooth occlusal surface on the exposed principal print-receiving surface and thereby producing a print of substantially only dental arch tooth occlusal surfaces having tooth print depressions with the maximum depth of the stamped imprint not appreciably exceeding twice the maximum depth of the tooth occlusal surface imprint depressions, removing the print-bearing pallet from the mouth, and cooling the pallet to harden the thermoplastic material of the pad to durable rigid hard strong condition dimensionally stable for preserving accurately the shape of the print of such tooth occlusal surfaces for indentification information-registering purposes.

5. A composite pallet for recording a print of dental arch tooth occlusal surfaces comprising a pad of thermoplastic material softenable by warming to a temperature of about 145° F. (62.78° C.) to a plasticized non-sticky condition deformable into intimate detailed contact with such tooth occlusal surfaces and quickly hardenable by cooling to durable rigid hard strong condition, dimensionally stable for preserving accurately the shape of the print of such tooth occlusal surfaces, and a tray of hard strong material which is not softenable at such softening temperature of said pad having a thickness approximately twice as great as the thickness of the tray and providing an exposed pincipal face for reception of a print of substantially only the dental arch tooth occlusal surfaces.

* * * * *